(12) United States Patent
Cryer

(10) Patent No.: US 6,582,460 B1
(45) Date of Patent: Jun. 24, 2003

(54) SYSTEM AND METHOD FOR ACCURATELY DEPLOYING A STENT

(75) Inventor: Brett W. Cryer, Sunnyvale, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 199 days.

(21) Appl. No.: 09/717,145

(22) Filed: Nov. 20, 2000

(51) Int. Cl.[7] .................................................. A61F 2/06
(52) U.S. Cl. ...................................................... 623/1.11
(58) Field of Search ............................... 623/1.11–1.16

(56) References Cited

U.S. PATENT DOCUMENTS

| | | |
|---|---|---|
| 5,037,392 A | 8/1991 | Hillstead |
| 5,059,169 A | 10/1991 | Zilber |
| 5,064,435 A | 11/1991 | Porter |
| 5,116,318 A | 5/1992 | Hillstead |
| 5,226,889 A | 7/1993 | Sheiban |
| 5,409,495 A | 4/1995 | Osborn |
| 5,476,476 A | 12/1995 | Hillstead |
| 5,645,559 A | 7/1997 | Hachtman et al. |
| 5,653,691 A | 8/1997 | Rupp et al. |
| 5,667,523 A | 9/1997 | Bynon et al. |
| 5,695,498 A | 12/1997 | Tower |
| 5,746,745 A | 5/1998 | Abele et al. |
| 6,126,685 A | 10/2000 | Lenker et al. |
| 6,217,586 B1 | 4/2001 | Mackenzie |
| 6,245,076 B1 | 6/2001 | Yan |
| 6,258,099 B1 | 7/2001 | Mareiro et al. |
| 6,270,521 B1 * | 8/2001 | Fischell et al. ............. 623/1.11 |
| 6,342,066 B1 * | 1/2002 | Toro et al. .................. 623/1.11 |
| 6,375,676 B1 * | 4/2002 | Cox ........................... 623/1.16 |
| 6,425,915 B1 * | 7/2002 | Khosravi et al. ........... 623/1.22 |
| 6,428,462 B1 * | 8/2002 | Mawad ........................... 600/3 |
| 6,443,980 B1 * | 9/2002 | Wang et al. ................. 623/1.11 |
| 6,461,383 B1 * | 10/2002 | Gesswein et al. .......... 623/6.11 |
| 6,471,718 B1 * | 10/2002 | Staehle et al. ............. 623/1.11 |
| 6,478,814 B2 * | 11/2002 | Wang et al. ................ 623/1.12 |

FOREIGN PATENT DOCUMENTS

WO     WO 95/11055     4/1995

* cited by examiner

Primary Examiner—David H. Willse
Assistant Examiner—Suzette J. Jackson
(74) Attorney, Agent, or Firm—Fulwider Patton Lee & Utecht, LLP

(57) ABSTRACT

A system used in a blood vessel when an interventional procedure is being performed in a stenosed or occluded region, which is capable of accurately treating an affected area in a blood vessel while preventing adverse effects for healthy tissue. The system includes a catheter which is positionable in a blood vessel at the interventional procedure site. The system further includes an interventional instrument such as a self-expandable stent which may be deployed in the blood vessel at the interventional procedure site. The system also includes an extendable member, adapted to be about the interventional instrument for delivery of the interventional instrument to the interventional procedure site, and to be retractable from extending about the interventional instrument for enabling the interventional instrument to expand at the interventional procedure site. The system further includes movement preventing elements, for preventing axial movement of the interventional instrument in a support region of a catheter elongated shaft, during retraction of the extendable member from extending about the interventional instrument, for enabling accurate deployment of the interventional instrument.

22 Claims, 3 Drawing Sheets

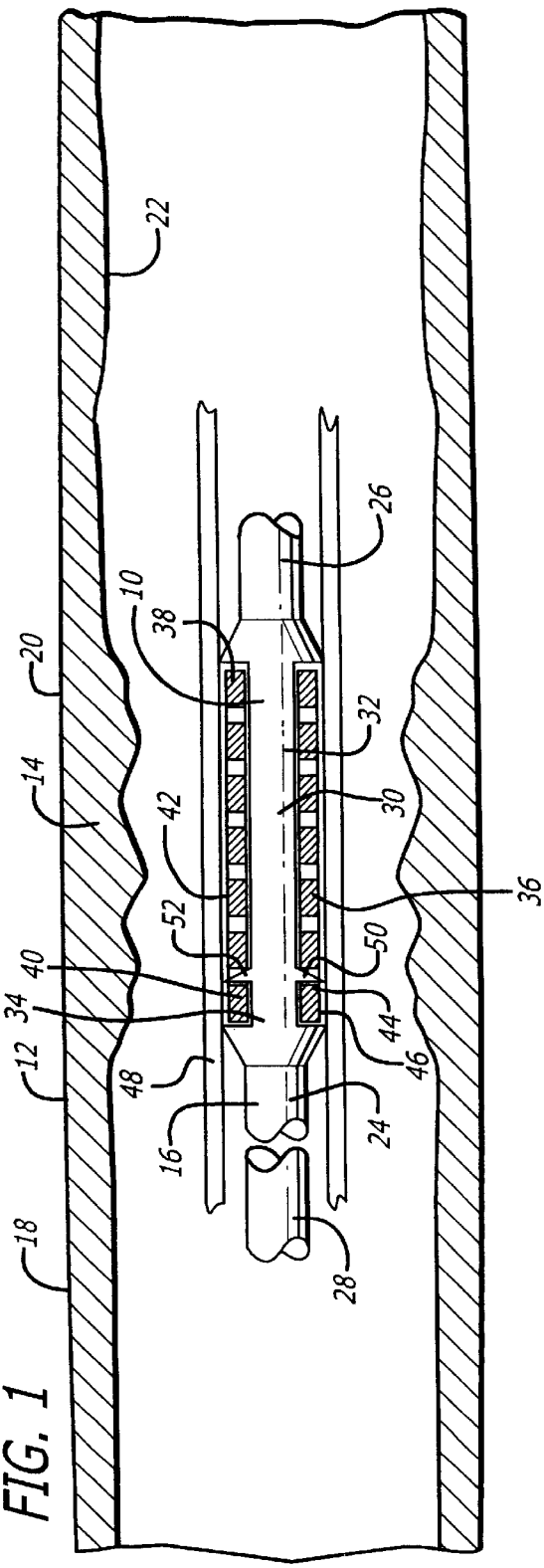
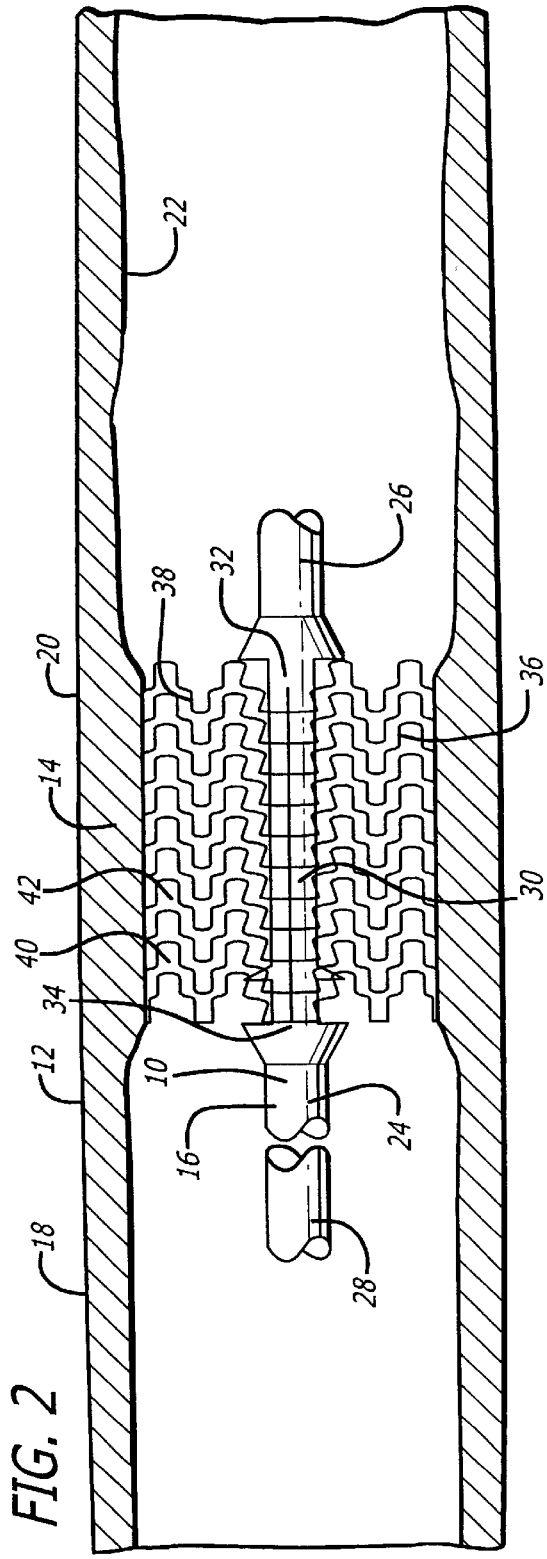
FIG. 1
FIG. 2

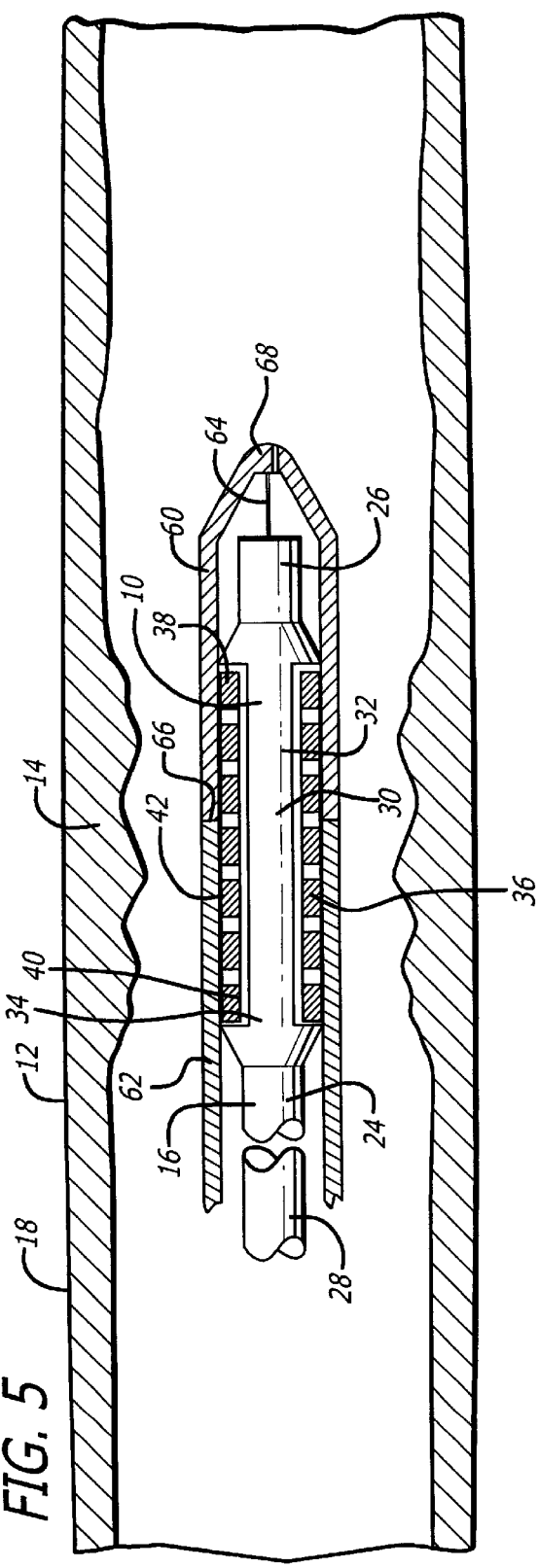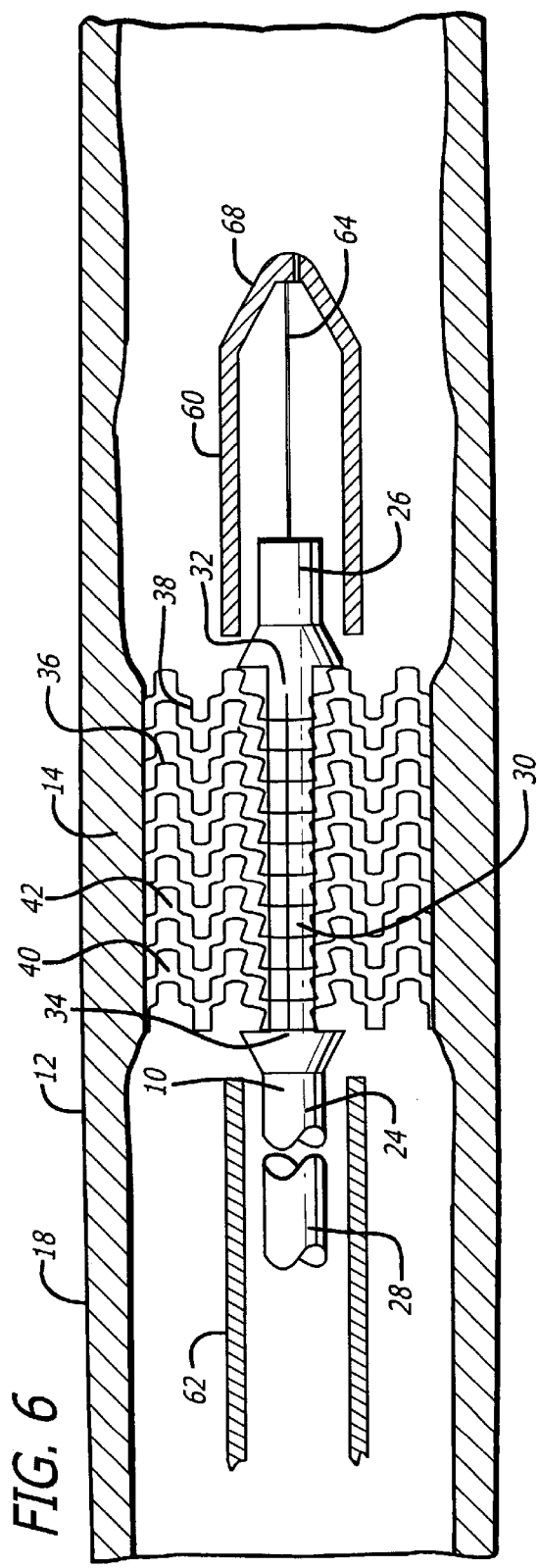

SYSTEM AND METHOD FOR ACCURATELY DEPLOYING A STENT

BACKGROUND OF THE INVENTION

The present invention relates generally to a system which can be used when an interventional procedure is being performed in a stenosed or occluded region of a blood vessel to substantially retain the unexpanded axial dimension of an expandable interventional instrument upon expansion thereof. The system of the present invention is particularly useful when performing stenting procedures in critical vessels, such as the carotid arteries.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter is usually used to capture the shaved plaque or thrombus from the blood stream during this procedure.

In another widely practiced procedure, the stenosis can be treated by placing an expandable interventional instrument such as an expandable stent into the stenosed region to hold open and sometimes expand the segment of blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

Prior art stents typically fall into two general categories of construction. The first type of stent is expandable upon application of a controlled force, often through the inflation of an expandable member such as an expandable balloon in a dilatation catheter which, upon inflation of the balloon or other expansion means, expands the compressed stent to a larger diameter to be left in place within the artery at the target site. The second type of stent is a self-expanding stent formed from, for example, shape memory metals or superelastic nickel-titanum (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

Self-expanding stents are typically delivered to an interventional procedure site for deployment thereof mounted on a delivery system and constrained in the sheath, to prevent the elastic nature of the self-expanding stent from causing it to expand prematurely. Once in position at the interventional procedure site, the sheath is retracted, enabling the stent to expand and deploy. However, there are problems associated with the retraction of the sheath for enabling deployment of the self-expanding stent. When the sheath is retracted during stent deployment, axial forces are generated in the stent when one end of the stent is fully open and the other end is still constrained. The stent is biased to slip out from under the sheath and finish deploying. An abrupt shortening that occurs as the stent deploys also generates axial forces. These axial forces can cause the stent to move in the distal direction during deployment and not properly cover the lesion as desired.

What has been needed is a reliable system and method for delivering an interventional device for treating stenosis in blood vessels which improve the accuracy of stent deployment over the lesion to be treated, while preventing axial movement of the stent during retracting of the sheath from extending thereabout. The system and method should be capable of enabling the stent to expand, while precisely placing the stent over the lesion to be treated. The system and method should be relatively easy for a physician to use. Moreover, such a system should be relatively easy to deploy and remove from the patient's vasculature. The inventions disclosed herein satisfy these and other needs.

SUMMARY OF INVENTION

The present invention provides a system and method for treating an entire affected area in a blood vessel during the performance of a therapeutic interventional procedure, such as a balloon angioplasty or stenting procedure, while preventing adverse effects to surrounding tissue. The present invention is particularly useful when performing an interventional procedure in vital arteries, such as the carotid arteries, including the main blood vessels leading to the brain or other vital organs. As a result, the present invention provides the physician with a higher degree of confidence that an entire lesion will be treated, and that healthy tissue will not be adversely affected by the stenting procedure.

The present invention enables an interventional procedure to be performed in a blood vessel at the site of a lesion at an interventional procedure site, such that axial movement of a stent is prevented during retraction of a sheath extending thereabout, and the stent is accurately deployed at the interventional procedure site to treat the lesion.

In the present invention, the system includes a catheter for positioning in a blood vessel at an interventional procedure site, an interventional device located at a distal end portion of the catheter for expanding and deploying in the blood vessel at the interventional procedure site, an extendable member adapted to be extendable about the interventional device and retractable relative thereto, and a movement preventing element for preventing axial movement of the interventional instrument during retraction of the extendable member.

In an embodiment of the present invention, the system includes a catheter, including an elongated shaft having a distal end portion adapted to be positioned in a blood vessel at an interventional procedure site, and a support region proximate the distal end of the elongated shaft. An interventional instrument is adapted to move between a collapsed and expanded position in the blood vessel at the interventional procedure site, and to be supported on the support region of the elongated shaft. An extendable member is adapted to be extendable about the interventional instrument for delivery of the interventional instrument to the interventional procedure site, and to be retractable from extending about the interventional instrument for enabling the interventional instrument to expand at the interventional procedure site. A movement preventing element, for preventing axial movement of the interventional instrument in the support region of the catheter elongated shaft, during retraction of the extendable member from extending about the interventional instrument, enables deployment of the interventional instrument.

In another embodiment of the present invention, the system includes a catheter, including an elongated shaft having a distal end portion adapted to be positioned in a blood vessel at an interventional procedure site, and a support region proximate the distal end of the elongated shaft. An interventional instrument is adapted to move between a collapsed and expanded position in the blood vessel at the interventional procedure site, and to be supported on the support region of the elongated shaft, which interventional instrument includes a distal portion and a proximal portion. A movement preventing element, for preventing axial movement of the interventional instrument in the support region of the catheter elongated shaft, includes a distal element, adapted to be extendable about the distal portion of the interventional instrument, and a proximal element, adapted to be extendable about the proximal portion of the interventional instrument. The distal element and the proximal element are adapted to be extendable about the interventional instrument for delivery of the interventional instrument to the interventional procedure site, and to be retractable from extending about the interventional instrument for enabling the interventional instrument to expand at the interventional procedure site. The movement preventing element is further adapted to prevent axial movement of the interventional instrument during retraction of the distal element and the proximal element.

Other features and advantages of the present invention will become more apparent from the following detailed description of the preferred embodiments of the invention, when taken in conjunction with the accompanying exemplary drawings.

BRIEF DESCRIPTION OF THE DRAWINGS

FIG. 1 is an elevational view, partially in section, depicting the system of the present invention disposed within the internal carotid artery of a patient, including a catheter, an extendable member in extended condition, an interventional instrument in unexpanded condition, and a first embodiment of a movement preventing element.

FIG. 2 is an elevational view, partially in section, similar to that shown in FIG. 1, depicting the system of the present invention, wherein the extendable member is retracted, and the interventional instrument is in expanded condition.

FIG. 5 is an elevational view, partially in section, depicting the system of the present invention, including a catheter, an interventional instrument in unexpanded condition, and a third embodiment of a movement preventing element including a pair of extendable members in unextended condition.

FIG. 6 is an elevational view, partly in section, similar to that shown in FIG. 5, depicting the system of the present invention, wherein the pair of extendable members are in retracted condition, and the interventional instrument is in expanded condition.

DETAILED DESCRIPTION OF THE PREFERRED EMBODIMENTS

Figure 3:
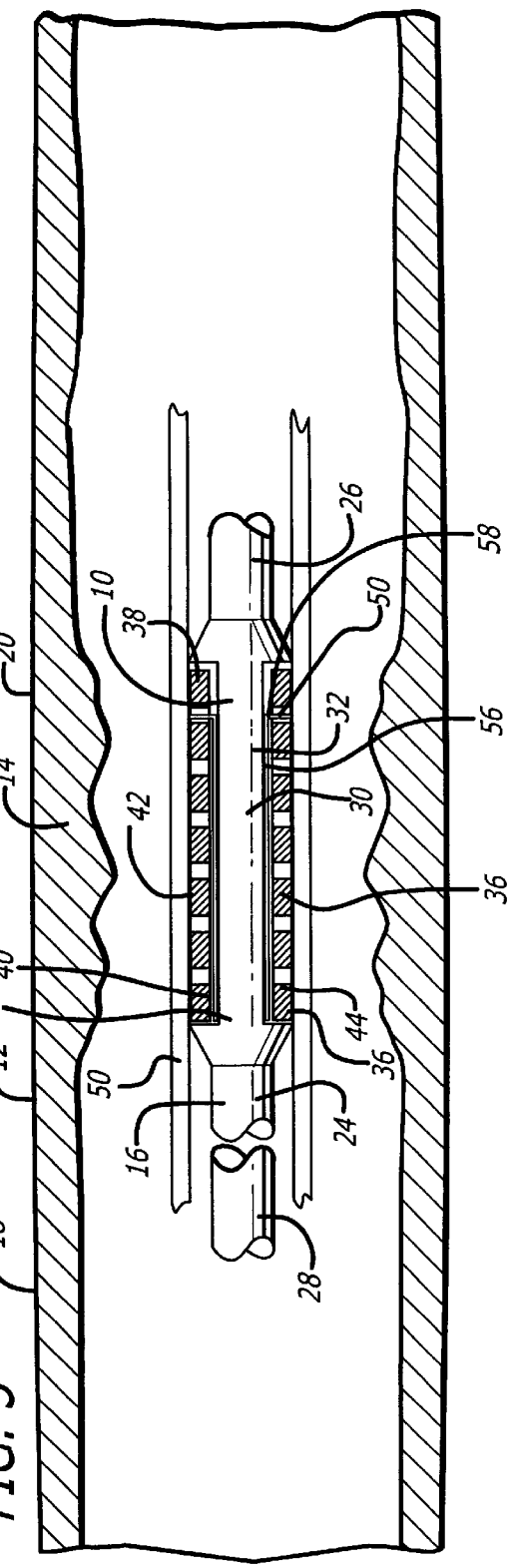
FIG. 3 is an elevational view, partially in section, depicting the system of the present invention, including a catheter, an extendable member in extended condition, an interventional instrument in unexpanded condition, and a second embodiment of a movement preventing element.

The present invention is directed to an improved system and method for efficiently and effectively enabling a therapeutic interventional procedure to be performed in a blood vessel at an interventional procedure site which is the site of a lesion. It is adapted to enable the delivery of a self-expandable interventional instrument to the interventional procedure site, and to enable expansion of the self-expandable interventional instrument at the interventional procedure site. It is further adapted to enable an extendable member to extend about the self-expandable interventional instrument for enabling delivery thereof to the interventional procedure site, and to enable retraction of the extendable member to enable the self-expandable interventional instrument to expand at the location of the stenosis at the interventional procedure site. It is also adapted to prevent axial movement of the self-expandable interventional instrument during retraction of the extendable member from extending thereabout for enabling deployment thereof. The embodiments of the improved system and method are illustrated and described herein by way of example only and not by way of limitation. While the present invention is described in detail as applied to the carotid arteries of the patient, those skilled in the art will appreciate that it can also be used in other body lumens as well, such as the coronary arteries, non-coronary arteries, renal arteries, saphenous veins and other peripheral arteries.

Referring now to the drawings, wherein like reference numerals denote like or corresponding parts throughout the drawing figures, and particularly to FIGS. 1–6, a system 10 is provided for enabling an interventional procedure to be performed in a blood vessel 12 at an area of treatment 14. The system 10 includes a catheter 16 adapted to enable the interventional procedure to be performed. As shown in FIGS. 1–6, the system 10 may be positioned on the catheter 16, and may be placed within the carotid artery 18 or other blood vessel of the patient on the catheter 16 and may be guided into position by a guide wire. The carotid artery 18 may have the area of treatment 14, which may comprise the interventional procedure site, wherein atherosclerotic plaque 20 may have built up against the inside wall 22, which decreases the diameter of the carotid artery 18. As a result, blood flow may be diminished through this area. The catheter 16 may include an elongated shaft 24 having a distal end 26 and a proximal end 28, and a support region 30 proximate the distal end 26 of the elongated shaft 24. The support region 30 includes a distal end 32 and a proximal end 34.

The therapeutic interventional procedure may comprise implanting an interventional instrument 36 at the interventional procedure site 14, to compress the build-up of plaque 20 of the stenosis against the inside wall 22, to increase the diameter of the occluded area 14 of the artery 18, and to help restore sufficient flow of blood to the downstream vessels leading to the brain. The interventional instrument 36 not only helps increase the diameter of the occluded area, but may help prevent restenosis in the area of treatment 14. The interventional instrument 36 is adapted to be supported on the support region 30 of the catheter 16, and to be expanded and deployed at the interventional procedure site 14. It includes an unexpanded axial dimension constituting the unexpanded length thereof, and is adapted to be expandable in a direction generally transverse to the axial dimension thereof. The interventional instrument 36 may comprise for example a self-expandable stent, the elastic nature of which enables self-expansion thereof absent constraint. The self-expandable stent 36 includes a distal end 38 and a proximal end 40, and includes a plurality of struts 42, each of which includes a distal end 44 and a proximal end 46.

An extendable member 48 is adapted to be extendable about the self-expandable stent 36 for delivery of the self-expandable stent 36 to the interventional procedure site 14. It is further adapted to be retractable from extending about the self-expandable stent 36 for enabling the self-expandable stent 36 to expand at the interventions procedure site 14. The extendable member 48 may comprise a sheath.

A movement preventing element 50 is adapted to prevent axial movement of the self-expandable stent 36 in the support region 30 of the catheter elongated shaft 24, during retraction of the extendable member 48 from extending about the self-expandable stent 36, for enabling deployment of the self-expandable stent 36 at the location of the stenosis at the interventional procedure site 14. The movement preventing element 50 may be adapted to prevent distal axial movement of the self-expandable stent 36.

In the embodiment of the invention illustrated in FIGS. 1–2, the movement preventing element 50 comprises portions 52 projecting from the support region 30 of the elongated shaft 24, so as to project distal to the struts 42 of the self-expandable stent 36 and prevent distal axial movement thereof The projecting portions 52 may comprise for example bumps, ridges, knobs or hooks. In the embodiment of the invention shown in FIGS. 3–4, the movement preventing element 50 comprises a pair of spring anchors, each of which includes a proximal end 54 and a distal end 56 therein. Each spring anchor 50 is adapted to be secured to the proximal end 34 of the support region 30 of the elongated shaft 24. The distal end 56 of each spring anchor 50 includes a portion 58 projecting therefrom distal to a strut 42 of the self-expandable stent 36. The projecting portion 58 may comprise a bump or a hook. Each spring anchor 50 is adapted to expand with and restrain the strut 42 to prevent distal axial movement of the self-expandable stent 36 during deployment thereof. The sheath 48 is further adapted to be advanced over the support region 30 of the elongated shaft 24 to recover the spring anchors 50 after deployment of the self-expanding stent 36.

In the embodiment of the invention seen in FIGS. 5–6, the movement preventing element 50 comprises a distal sheath 60, adapted to be extendable about and retractable from extending about the distal end 38 of the self-expandable stent 36, and a proximal sheath 62, adapted to be extendable about and retractable from extending about the proximal end 40 of the self-expandable stent 36, so as to provide a mid-stent articulation point, and prevent axial movement of the self-expandable stent 36. The middle-outward deployment is adapted to reduce jumping of the stent 36, since axial forces generated would be equal and opposite, counteracting each other and reducing any tendency of the stent 36 to shift. The system 10 further includes an element 64 for enabling the distal sheath 60 to be retracted from extending about the distal end 38 of the self-expandable stent 36, and an element for enabling the proximal sheath 62 to be retracted from extending about the proximal end 40 of the self-expandable stent 36. The distal sheath retraction-enabling element 64 and the proximal sheath retraction-enabling element are preferably adapted to enable retracting movements at substantially equal rates of the distal sheath 60 and the proximal sheath 62. The self-expandable stent 36, further includes a medial portion 66. The distal sheath 60 includes a distal end 68, and the distal sheath retracting-enabling element 64 is adapted to be connected to the distal end 68 of the distal sheath 60, and to be controlled from the proximal end 28 of the elongated shaft 24. The distal sheath retraction-enabling element 64 may comprise for example a mandrel or hypo tube, or a cylindrical or tubular member extending under the self-expandable stent 36 and connected to the distal end 68 of the distal sheath 60.

In use, as illustrated in FIGS. 1–6, the system 10 may be positioned in the patient's vasculature utilizing any one of a number of different methods. In one preferred method of positioning, the catheter elongated shaft support region 30, the stent 36 supported thereon, and the sheath 48 extending thereabout, may be placed in the blood vessel 12 by utilizing the catheter 16 and the sheath 48, which are inserted into the patient's vasculature and manipulated by the physician to the area of treatment 14 so as to cross the stenosis in the blood vessel 12. The sheath 48 may then be retracted from extending about the stent 36, so as to enable the stent 36 to expand at the interventional procedure site 14. As the sheath 48 is retracted, the movement preventing element 50 in the catheter elongated shaft support portion 30 is adapted to prevent axial movement and expansion of the stent 36 during retraction of the sheath 48, so as to enable deployment of the stent 36 at the location of the stenosis at the interventional procedure site 14 upon retraction of the sheath 48.

In the embodiment of the invention illustrated in FIGS. 1–2, the projecting portions 52 in the catheter elongated shaft support region 30 prevent distal axial movement of the stent 36 during retraction of the sheath 48 in the proximal direction. In the embodiment of the invention shown in FIGS. 3–4, the projecting portion 52 at the proximal end 54 of the spring 50 prevents a distal axial movement of the stent 36 during retraction of the sheath 48 in the proximal direction. In the embodiment of the invention seen in FIGS. 5–6, the retraction of the distal sheath 60 in the distal direction and the retraction of the proximal sheath 62 in the proximal direction, from the medial portion 64 of the stent 36 outwardly towards the distal end 38 and the proximal end 40 of the stent 36, prevent expansion of the stent 36 during retraction of the distal sheath 60 in the distal direction and the retraction of the proximal sheath 62 in the proximal direction.

Figure 4:
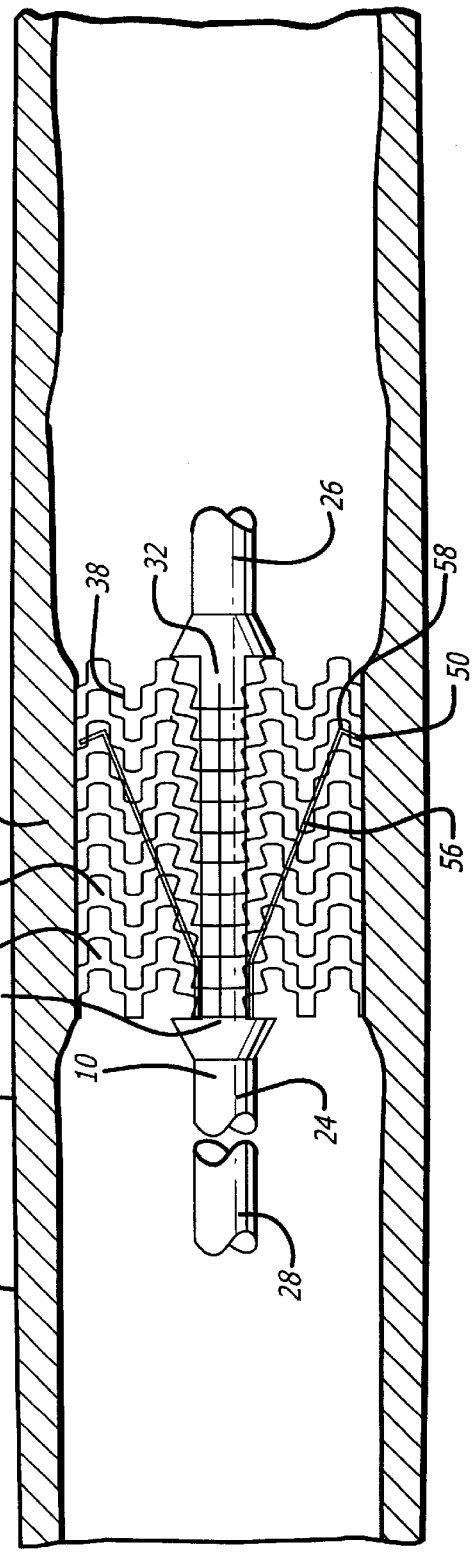
FIG. 4 is an elevational view, partially in section, similar to that shown in FIG. 3, depicting the system of the present invention, wherein the extendable member is retracted, and the interventional instrument is in expanded condition.

It should be appreciated that the particular embodiments of the movement preventing element 50 are capable of being positioned in the blood vessel 12. However, other forms of the movement preventing element 50 may be utilized with the present invention without departing from the spirit and scope of the invention. For example, the movement preventing element 50 may further be comprised of other forms of material. Additionally, while the movement preventing element 50 is shown as in various shapes in the embodiments herein, it can be formed in any one of a number of different shapes depending upon the construction desired. Also, the portions 52 of the movement preventing element 50 which project from the support region 30 of the catheter elongated shaft 24, as shown in FIGS. 1–2, which may comprise bumps, ridges, knobs, or hooks, for example may be comprised of a separate metallic or polymer piece adapted to be attached to the support region 30, or may be formed in the support region 30 by heat-processing thereof Further, the spring anchor of the movement enabling element 50, as shown in FIGS. 3–4, for example may be comprised of a material sufficiently elastic to expand with the stent 36, and to be safely recoverable, such as steel, nitinol, or polymer. The portion 58 of the spring anchor 50 may be comprised for example of material different from the material of the spring anchor 50, and may be attached to the distal end 56 of the spring anchor 50. The distal sheath 60 and the proximal sheath 62 as seen in FIGS. 5–6, may each for example be comprised of a material different from the other, adapted to provide enhanced delivery properties, wherein the distal sheath 60 may be softer or may include an atraumatic tip.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the effectiveness of performing interventional procedures by preventing axial movement of the self-expandable stent during retraction of the extendable member, to enable the self-expandable stent to expand at the location of the stenosis at the interventional procedure site. Further modifications and improvements may additionally be made to the system and method disclosed herein without the departing from the scope of the invention. Accordingly, it is not intended that the invention be limited, except as by the appended claims.

What is claimed:

1. A system for enabling an interventional procedure to be performed in a blood vessel at an interventional procedure site, comprising:
    A catheter, including an elongated shaft having a distal end portion adapted to be positioned in a blood vessel at an interventional procedure site, and s support region proximate the distal end of the elongated shaft;
    an interventional instrument, adapted to move between a collapsed and expanded position in the blood vessel at the interventional procedure site, and adapted to be supported on the support region of the elongated shaft;
    an extendable member, adapted to be extendable about the interventional instrument for delivery of the interventional instrument to the interventional procedure site, and to be retractable from extending about the interventional instrument for enabling the interventional instrument to expand at the interventional procedure site; and
    a movement preventing element, for contacting the interventional instrument and preventing axial movement of the interventional instrument in the support region of the catheter elongated shaft, curing retraction of the extendable member from extending about the interventional instrument, for enabling deployment of the interventional instrument, wherein the movement preventing element is integral with and projects from the catheter support region.

2. The system of claim 1, wherein the extendable member comprises sheath, and the interventional instrument comprises a self-expandable stent, the elastic nature of which enables self-expansion thereof absent constraint.

3. The system of claim 2, wherein the movement preventing element s adapted to prevent distal axial movement of the self-expandable stent.

4. The system of claim 2, wherein the self-expandable stent includes struts therein, and the movement preventing element comprises portions projecting from the support region of the elongated shaft, so as to project distal to the self-expandable stent struts and prevent distal movement thereof.

5. A system for enabling an interventional procedure to be performed in a blood vessel at an interventional procedure site, comprising:
    a catheter, including an elongated shaft having a distal end portion adapted to be positioned in a blood vessel at an interventional procedure site, and a support region proximate the distal end of the elongated shaft;
    an interventional instrument, adapted to move between a collapsed and expanded position in the blood vessel at the interventional procedure site, and adapted to be supported on the support region of the elongated shaft, which interventional instrument includes a distal portion and a proximal portion; and
    a movement preventing element, for preventing axial movement of the interventional instrument in the support region of the catheter elongated shaft, comprising a distal extendable element, adapted to be extendable about the distal portion of the interventional instrument, and a proximal extendable element, adapted to be extendable about the proximal portion of the interventional instrument, wherein the distal extendable element and the proximal extendable element are adapted to be extendable about the interventional instrument for delivery of the interventional instrument to the interventional procedure site, and to be retractable from extending about the interventional instrument for enabling the interventional instrument to expand at the interventional procedure site, and wherein the movement preventing element is adapted to prevent axial movement of the interventional instrument during retraction of the distal extendable element and the proximal extendable element.

6. The system of claim 5, wherein the distal extendable element comprises a distal sheath, the proximal extendable element comprises a proximal sheath, and the interventional instrument comprises a self-expandable stent, the elastic nature of which enables self-expansion thereof absent constraint.

7. The system of claim 6, further comprising an element for enabling the distal sheath to be retracted from extending about the distal portion of the self-expandable stent.

8. The system of claim 6, further comprising an element for enabling the proximal sheath to be retracted from extending about the proximal portion of the self-expandable stent.

9. The system of claim 6, wherein the self-expandable stent further includes a medial portion, the distal sheath is adapted to be retractable from extending about the self-expandable stent from the medial portion of the self-expandable stent to the distal portion thereof, and the proximal sheath is adapted to be retractable from extending abut the self-expandable stent from the medial portion of the self-expandable stent to the proximal portion thereof.

10. The system of claim 7, wherein the catheter elongated shaft includes a proximal end, and the distal sheath includes a distal end, further comprising an element for enabling control of distal movement of the distal sheath from the proximal end of the catheter elongated shaft, wherein the control-enabling element is adapted to be connected to the distal end of the distal sheath.

11. A system for enabling an interventional procedure to be performed in a blood vessel at an interventional procedure site, comprising:

a catheter, including an elongated shaft having a distal end portion adapted to be positioned in a blood vessel at an interventional procedure site, and a support region proximate the distal end of the elongated shaft;

interventional procedure performing means for performing an interventional procedure, adapted to move between a collapsed and expanded position in the blood vessel at the interventional procedure site, adapted to be supported on the support region of the elongated shaft;

extending means for extending about the interventional procedure performing means for delivery of the interventional procedure performing means to the interventional procedure site, and for retracting from extending about the interventional procedure performing means for enabling the interventional procedure performing means to expand at the interventional procedure site; and axial movement preventing means for preventing axial movement of the interventional procedure performing means in the support region of the catheter elongated shaft, during retraction of the extending means from extending about the interventional procedure performing means, for enabling deployment of the interventional procedure performing means, wherein the axial movement preventing means are integral with and project from the catheter support region.

12. The system of claim 11, wherein the extending means comprise a sheath, and the interventional procedure performing means comprise a self-expandable stent, the elastic nature of which enables self-expansion thereof absent constraint.

13. The system of claim 12, wherein the axial movement preventing means are adapted to prevent distal axial movement of the self-expandable stent.

14. A system for enabling an interventional procedure to be performed in a blood vessel at an interventional procedure site, comprising:

a catheter, including an elongated shaft having a distal end portion adapted to be positioned in a blood vessel at an interventional procedure site, and a support portion proximate the distal end of the elongated shaft;

interventional procedure performing means for performing an interventional procedure, adapted to move between a collapsed and expanded position in the blood vessel at the interventional procedure site, adapted to be supported on the support region of the elongated shaft, which interventional procedure performing means include a distal portion and a proximal portion;

axial movement preventing means for preventing axial movement of the interventional procedure performing means in the support region of the catheter elongated shaft, during retraction of the sheath from extending about the interventional procedure performing means, for enabling deployment of the interventional procedure performing means, comprising distal extendable means for extending about the distal portion of the interventional procedure performing means, and proximal extendable means for extending about the proximal portion of the interventional procedure performing means, wherein the distal extendable means and the proximal extendable means are adapted to be extendable about the interventional procedure performing means for delivery of the interventional procedure performing means to the interventional procedure site, and to be retractable from extending about the interventional procedure performing means for enabling the interventional procedure performing means to expand at the interventional procedure site.

15. The system of claim 14, wherein the distal extendable means comprise a distal sheath, the proximal extendable means comprise a proximal sheath, and the interventional procedure performing means comprise a self-expandable stent, the elastic nature of which enables self-expansion thereof absent constraint.

16. A method of enabling an interventional procedure to be performed in a blood vessel at an interventional procedure site, in a system which comprises a catheter, including an elongated shaft having a distal end portion adapted to be positioned in a blood vessel at an interventional procedure site, and a support region proximate the distal end of the elongated shaft, an interventional instrument, adapted to move between a collapsed and expanded position in the blood vessel at the interventional procedure site, and adapted to be supported on the support region of the elongated shaft, an extendable member, adapted to be extendable about the interventional instrument for delivery of the interventional instrument to the interventional procedure site, and to be retractable from extending about the interventional instrument for enabling the interventional instrument to expand at the interventional procedure site, and a movement preventing element for contacting the interventional instrument and preventing axial movement of the interventional instrument in the support region of the catheter elongated shaft, during retraction of the extendable member from extending about the interventional instrument, for enabling deployment of the interventional instrument, wherein the movement preventing element is integral with and projects from the catheter support region, and wherein the method comprises:

positioning the catheter elongated shaft in the interventional procedure site such that the support region and the interventional instrument supported thereon in the distal end portion of the catheter elongated shaft are positioned at the interventional procedure site;

retracting the extendable member from extending about the interventional instrument so as to enable the interventional instrument to expand at the interventional procedure site;

preventing axial movement of the interventional instrument in the support region of the catheter elongated shaft by the movement preventing element which is integral with and projecting from the catheter support region and contacting the interventional instrument while retracting the extendable member; and enabling deployment of the interventional instrument at the interventional procedure site upon retraction of the extendable member.

17. A method of enabling an interventional procedure to be performed in a blood vessel at an interventional procedure site, in a system which comprises a catheter, including an elongated shaft having a distal end portion adapted to be positioned in a blood vessel at an interventional procedure site, and a support region proximate the distal end of the elongated shaft, an interventional instrument, adapted to move between a collapsed and expanded position in the blood vessel at the interventional procedure site, and adapted to be supported on the support region of the elongated shaft, which interventional instrument includes a distal portion and a proximal portion, and a movement preventing element for preventing axial movement of the interventional instrument in the support portion of the catheter elongated shaft, comprising a distal extendable element, adapted to be extendable about the distal portion of the interventional instrument, and a proximal extendable element, adapted to be extendable about the proximal portion of the interventional instrument, wherein the distal extendable element and the proximal extendable element are adapted to be extendable about the interventional instrument for delivery of the interventional instrument to the interventional procedure site, and to be retractable from extending about the interventional instrument for enabling the interventional instrument to expand at the interventional procedure site, and wherein the movement preventing element is adapted to prevent axial movement of the interventional instrument during retraction of the distal extendable element and the proximal extendable element, wherein the method comprises:

positioning the catheter elongated shaft in the interventional procedure site such that the support region and the interventional instrument supported thereon in the distal end portion of the catheter elongated shaft are positioned at the interventional procedure site;

retracting the distal extendable element in the proximal direction from extending about the distal end of the interventional instrument and the proximal extendable element in the distal direction from extending about the proximal end of the interventional instrument, so as to prevent axial movement and expansion of the interventional instrument in the support portion of the catheter elongated shaft while retracting the distal extendable element and the proximal extendable element; and enabling deployment of the interventional instrument at the interventional procedure site upon retraction of the distal extendable element and the proximal extendable element.

18. A method of enabling an interventional procedure to be performed in a blood vessel at an interventional procedure site, in a system which comprises a catheter, including an elongated shaft having a distal end portion adapted to be positioned in a blood vessel at an interventional procedure site, and a support region proximate the distal end of the elongated shaft, interventional procedure performing means for performing an interventional procedure, adapted to move between a collapsed and expanded position in the blood vessel at the interventional procedure site, adapted to be supported on the support region of the elongated shaft, extending means for extending about the interventional procedure performing means for delivery of the performing means to the interventional procedure site, and for retracting from extending about the interventional procedure performing means for enabling the interventional procedure performing means to expand at the interventional procedure site, and axial movement preventing means for preventing axial movement of the interventional procedure performing means in the support portion of the catheter elongated shaft, during retraction of the extending means from extending about the interventional procedure performing means, for enabling deployment of the interventional procedure performing means, wherein the movement preventing element is integral with and projects from the catheter support region, and wherein the method comprises:

positioning the catheter elongated shaft in the interventional procedure site such that the support region and the interventional procedure performing means supported thereon in the distal end portion of the catheter elongated shaft are positioned at the interventional procedure site;

retracting the extending means from extending about the interventional procedure performing means so as to enable the interventional procedure performing means to expand at the interventional procedure site;

preventing axial movement of the interventional procedure performing means in the support portion of the catheter elongated shaft by the movement preventing element which is integral with and projecting from the catheter support region and contacting the interventional instrument while retracting the extending means; and enabling deployment of the interventional procedure performing means at the interventional procedure site upon retraction of the extending means.

19. A system for enabling an interventional procedure to be performed in a blood vessel at an interventional procedure site, comprising:

a catheter, including an elongated shaft having a distal end portion adapted to be positioned in a blood vessel at an interventional procedure site, and a support region proximate the distal end of the elongated shaft;

an interventional instrument, adapted to move between a collapsed and expanded position in the blood vessel at the interventional procedure site, and adapted to be supported on the support region of the elongated shaft, comprising a self-expandable stent, the elastic nature of which enables self-expansion thereof absent constraint, wherein the self-expandable stent includes a distal end including distal end struts therein;

an extendable member, adapted to be extendable about the interventional instrument for delivery of the interventional instrument to the interventional procedure site, and to be retractable from extending about the interventional instrument for enabling the interventional instrument to expand at the interventional procedure site, comprising a sheath; and a movement preventing element, for preventing axial movement of the interventional instrument in the support region of the catheter elongated shaft, during retraction of the extendable member from extending about the interventional instrument, for enabling deployment of the interventional instrument, comprising a spring anchor which includes a proximal and a distal end, wherein the spring anchor is adapted to be secured to the proximal end of the support region of the elongated shaft, and the distal end of the spring anchor includes a portion projecting therefrom distal to a strut of the self-expandable stent, and is adapted to expand with and restrain the strut to prevent distal movement of the self-expandable stent during deployment thereof.

20. The system of claim 19, wherein the sheath is further adapted to be advanced over the support region of the elongated shaft to recover the spring anchor after deployment of the self-expanding stent.

21. The system of claim 19, wherein the projecting portion comprises a bump.

22. The system of claim 19, wherein the projecting portion comprises a hook.

* * * * *